US012805784B2

(12) United States Patent
Udagawa et al.

(10) Patent No.: US 12,805,784 B2
(45) Date of Patent: Nov. 24, 2026

(54) TRANSPARENT ELECTRODE AND MEASURING DEVICE

(71) Applicant: SAMSUNG ELECTRONICS CO., LTD., Suwon-si (KR)

(72) Inventors: Kazuo Udagawa, Yokohama (JP); Atsushi Sato, Yokohama (JP); Injo Jeong, Suwon-si (KR); Jongseok Yoon, Suwon-si (KR); Taehoon Lee, Suwon-si (KR); Yoshihiro Yokote, Yokohama (JP)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 181 days.

(21) Appl. No.: 18/742,630

(22) Filed: Jun. 13, 2024

(65) Prior Publication Data

US 2024/0415437 A1 Dec. 19, 2024

Related U.S. Application Data

(63) Continuation of application No. PCT/KR2024/008087, filed on Jun. 12, 2024.

(30) Foreign Application Priority Data

Jun. 13, 2023 (JP) ................................ 2023-096739

(51) Int. Cl.

*A61B 5/263* (2021.01)
*A61B 5/256* (2021.01)
*H01B 5/14* (2006.01)

(52) U.S. Cl.

CPC ............. *A61B 5/263* (2021.01); *A61B 5/256* (2021.01); *H01B 5/14* (2013.01)

(58) Field of Classification Search

CPC ............ A61B 5/263; A61B 5/256; H01B 5/14
See application file for complete search history.

(56) References Cited

U.S. PATENT DOCUMENTS

| | | | |
|---|---|---|---|
| 10,490,317 | B2 | 11/2019 | Kim et al. |
| 2005/0034755 | A1 | 2/2005 | Okada et al. |
| 2011/0158845 | A1 | 6/2011 | Tokuchi et al. |

(Continued)

FOREIGN PATENT DOCUMENTS

| | | | |
|---|---|---|---|
| CN | 106910794 | A | 6/2017 |
| CN | 107393979 | A | 11/2017 |

(Continued)

OTHER PUBLICATIONS

Do Young, Ho, Translation of KR-20200122447-A, 2020 (Year: 2020).*

(Continued)

*Primary Examiner* — Adam Z Minchella
(74) *Attorney, Agent, or Firm* — Sughrue Mion, PLLC

(57) ABSTRACT

A transparent electrode disposed on the insulating substrate, the conductive layer including at least one of a metal layer or a metal oxide layer, a transparent electrode layer including $SnO2$ as a main component; and a current collector on at least a portion of a side surface of the transparent electrode layer, the current collector being electrically connected to the transparent electrode layer and the conductive layer.

9 Claims, 12 Drawing Sheets

(56) References Cited

U.S. PATENT DOCUMENTS

| | | | | |
|---|---|---|---|---|
| 2012/0022385 | A1* | 1/2012 | Shimuta | A61B 5/302 600/509 |
| 2012/0157807 | A1* | 6/2012 | Virtanen | A61B 5/259 600/372 |
| 2014/0035193 | A1 | 2/2014 | Haishi et al. | |
| 2015/0207080 | A1* | 7/2015 | Yoshida | B05D 1/36 427/125 |
| 2016/0299609 | A1 | 10/2016 | Sugitani et al. | |
| 2018/0024388 | A1* | 1/2018 | Shingai | B32B 9/045 345/173 |
| 2018/0046005 | A1 | 2/2018 | Yoon et al. | |
| 2018/0098422 | A1 | 4/2018 | Kuchiyama et al. | |
| 2019/0081190 | A1 | 3/2019 | Naito et al. | |
| 2022/0123244 | A1* | 4/2022 | Ryu | H01B 1/08 |
| 2023/0025098 | A1 | 1/2023 | Shida et al. | |

FOREIGN PATENT DOCUMENTS

| | | | | |
|---|---|---|---|---|
| EP | 3 185 249 | B1 | 11/2020 | |
| JP | 2001-13531 | A | 1/2001 | |
| JP | 4493001 | B2 | 6/2010 | |
| JP | 4815838 | B2 | 11/2011 | |
| JP | 2012-43835 | A | 3/2012 | |
| JP | 2012-59417 | A | 3/2012 | |
| JP | 2017-107707 | A | 6/2017 | |
| JP | 2017-191770 | A | 10/2017 | |
| JP | 2019-34548 | A | 3/2019 | |
| JP | 6782211 | B2 | 11/2020 | |
| JP | 2022-136143 | A | 9/2022 | |
| KR | 10-2004-0095320 | A | 11/2004 | |
| KR | 10-2014-0090876 | A | 7/2014 | |
| KR | 10-2015-0113911 | A | 10/2015 | |
| KR | 10-2020-0122446 | A | 10/2020 | |
| KR | 10-2020-0122447 | A | 10/2020 | |
| KR | 20200122447 | A * | 10/2020 | C23C 28/32 |
| WO | 2010/004783 | A1 | 1/2010 | |

OTHER PUBLICATIONS

Translation of KR-20200122447-A, 2020 (Year: 2020).*

International Search Report (PCT/ISA/210) issued Sep. 30, 2024 by the International Searching Authority in International Patent Application No. PCT/KR2024/008087.

Written Opinion (PCT/ISA/237) issued Sep. 30, 2024 by the International Searching Authority in International Patent Application No. PCT/KR2024/008087.

Extended European Search Report issued Oct. 27, 2025 by the European Patent Office for EP Patent Application No. 24823709.1.

* cited by examiner

| Sample | Conductive layer | | Transparent electrode layer | | Current collector | Physical durability | Chemical durability | Conductivity | Transparency |
|---|---|---|---|---|---|---|---|---|---|
| | Material | Film thickness (nm) | Material | Film thickness (nm) | | | | | |
| Embodiment 1 | First metal/ second metal laminated (with opening) | 10 / 20 | $SnO_2$ | 30 | Conductive layer co-used | × | ○ | ○ | ○ |
| | | | | 60 | | △ | ○ | ○ | ○ |
| | | | | 100 | | ○ | ○ | ○ | ○ |
| | | | | 200 | | ○ | ○ | ○ | △ |
| | | | | 300 | | △ | ○ | ○ | × |
| Embodiment 2 | Second metal (with no opening) | 5 | $SnO_2$ | 30 | First metal 30nm | ○ | ○ | ○ | ○ |
| | | | | 60 | | ○ | ○ | ○ | ○ |
| | | | | 100 | | ○ | ○ | ○ | △ |
| | | | | 200 | | ○ | ○ | ○ | △ |
| | | | | 300 | | △ | ○ | ○ | × |
| Embodiment 3 | Second metal (with opening) | 30 | $SnO_2$ | 30 | | × | ○ | ○ | ○ |
| | | | | 60 | | △ | ○ | ○ | ○ |
| | | | | 100 | | ○ | ○ | ○ | ○ |
| | | | | 200 | | ○ | ○ | ○ | ○ |
| | | | | 300 | | △ | ○ | ○ | × |

FIG. 9

| Sample | Conductive layer | | Transparent electrode layer | | Current collector | Physical durability | Chemical durability | Conductivity | Transparency |
|---|---|---|---|---|---|---|---|---|---|
| | Material | Film thickness (nm) | Material | Film thickness (nm) | | | | | |
| Embodiment 4 | Metal oxide | 100 | $SnO_2$ | 30 | First metal 30nm | ○ | ○ | ○ | ○ |
| | | | | 60 | | ○ | ○ | ○ | ○ |
| | | | | 100 | | ○ | ○ | ○ | ○ |
| | | | | 200 | | ○ | ○ | ○ | △ |
| | | | | 300 | | △ | ○ | ○ | × |
| Embodiment 5 | Second metal (with opening) / metal oxide | 30 / 100 | $SnO_2$ | 30 | | ○ | ○ | ○ | ○ |
| | | | | 60 | | ○ | ○ | ○ | ○ |
| | | | | 100 | | ○ | ○ | ○ | ○ |
| | | | | 200 | | ○ | ○ | ○ | △ |
| | | | | 300 | | △ | ○ | ○ | × |
| Embodiment 6 | First metal/ second metal laminated (with opening) | 10 / 20 | $SnO_2$ + F | 30 | Conductive layer co-used | × | ○ | ○ | ○ |
| | | | | 60 | | △ | ○ | ○ | ○ |
| | | | | 100 | | ○ | ○ | ○ | ○ |
| | | | | 200 | | ○ | ○ | ○ | △ |
| | | | | 300 | | ○ | ○ | ○ | × |

FIG. 10

| Sample | Conductive layer | | Transparent electrode layer | | Current collector | Physical durability | Chemical durability | Conductivity | Transparency |
|---|---|---|---|---|---|---|---|---|---|
| | Material | Film thickness (nm) | Material | Film thickness (nm) | | | | | |
| Comparative example 1 | Second metal (with opening) | 300 | $SnO_2$ | 30 | Conductive layer co-used | × | × | ○ | ○ |
| | | | | 60 | | △ | × | ○ | ○ |
| | | | | 100 | | ○ | × | ○ | ○ |
| | | | | 200 | | ○ | × | ○ | △ |
| | | | | 300 | | △ | × | ○ | × |
| Comparative example 2 | Metal oxide | 100 | $SnO_2$ | 30 | Conductive layer co-used | ○ | × | ○ | ○ |
| | | | | 60 | | ○ | × | ○ | ○ |
| | | | | 100 | | ○ | × | ○ | △ |
| | | | | 200 | | ○ | × | ○ | × |
| | | | | 300 | | △ | × | ○ | × |
| Comparative example 3 | - | - | $SnO_2$ | 30 | Conductive layer co-used | △ | ○ | × | ○ |
| | | | | 60 | | ○ | ○ | × | ○ |
| | | | | 100 | | ○ | ○ | × | ○ |
| | | | | 200 | | ○ | ○ | △ | △ |
| | | | | 300 | | △ | ○ | △ | × |
| Comparative example 4 | Metal oxide | 100 | - | - | Conductive layer co-used | ○ | × | ○ | ○ |

FIG. 11

| Sample | Ra (nm) | Rz (nm) | Particle size (nm) | Film density ($g\ cm^{-3}$) | Durability |
|---|---|---|---|---|---|
| Embodiment A | 1.2 | 13.9 | 40-50 | 7.0 | ○ |
| Embodiment B | 3.3 | 33.2 | 30-40 | 6.9 | ○ |
| Embodiment C | 8.6 | 118.7 | 50-200 | 6.6 | × |

FIG. 12

TRANSPARENT ELECTRODE AND MEASURING DEVICE

CROSS-REFERENCE TO RELATED APPLICATION(S)

This application is a by-pass continuation application of International Application No. PCT/KR2024/008087, filed on Jun. 12, 2024, which is based on and claims priority to Japanese Patent Application No. 2023-096739, filed on Jun. 13, 2023, in the Japan Patent Office, the disclosures of which are incorporated by reference herein their entireties.

BACKGROUND

1. Field

The disclosure relates to a transparent electrode that may be equipped in a measuring device, such as a wearable device, and a measuring device equipped with the transparent electrode.

2. Description of Related Art

In related art, a display unit includes a transparent front substrate having a first transparent electrode on an inner surface in a case with a back cover, a transparent rear substrate having a second transparent electrode on the inner surface, and a display cell including two substrate fixing frames forming a closed space between the substrates (the transparent front substrate and the transparent rear substrate) and displaying temporal information on the display cell by a control means.

Recently, as interest in health increases, demand and use of smart wearable devices that may monitor physical health conditions in real-time are rapidly expanding.

Electrical measurement and optical measurement are two general methods for obtaining biometric information, as equipped in a wearable device. When performing optical measurement, the external components of the optical measurement unit require high transmittance at the wavelength used for measurement. In the case of electrical measurement, the electrical measurement unit typically includes metal electrodes and is thus optically non-transmissive. Therefore, when mounting both the electrical measurement unit and the optical measurement unit in the limited exterior area of the wearable device, the degree of design freedom is reduced due to difficulty to place them with one overlapping the other.

When equipping the above-mentioned two types of measurement units in a wearable device, it may be considered to use well-known transparent electrodes. Typically, the transparent electrode is formed of a material, such as metal oxide (ITO), which has both high conductivity and light transparency, like the conventional transparent electrode. However, this type of transparent electrode is typically placed in a closed space, such as inside a case, and durability is not taken into consideration. Therefore, it may not be placed on the outermost surface of the device, and the degree of design freedom cannot be enhanced.

SUMMARY

To address the issues with the conventional transparent electrode, the disclosure proposes a novel transparent electrode that has physical and chemical durability while maintaining transparency, which were not considered in the conventional transparent electrode.

The disclosure provides a transparent electrode and a measuring device capable of providing physical and chemical durability for withstanding placement on the outermost surface of a device while securing transparency and enhancing the degree of design freedom of a device by combined use of an electrical measurement unit and an optical measurement unit.

The foregoing objectives of the present embodiments are achieved by any one of (1) to (7) below:

(1) a transparent electrode formed on an insulating substrate and electrically connectable to an object in contact with the object. The transparent electrode comprising a conductive layer disposed on the insulating substrate and including a metal oxide layer having at least one of a metal layer or a metal oxide layer, a transparent electrode layer including $SnO_2$ as a main component and a current collector disposed on at least a portion of a side surface of the transparent electrode layer and electrically (or operatively) connected to the transparent electrode layer and the conductive layer;

(2) The transparent electrode of (1), wherein, when the metal layer of the conductive layer has a film thickness of more than 5 nm, the metal layer of the conductive layer is formed so that a projected area with respect to the insulating substrate when looking down at the metal layer is 30% or less of the area of the insulating substrate;

(3) The transparent electrode of (1) or (2), wherein the metal layer includes one or more elements selected from among Ag, Al, Cr, Cu, Au, Pt, Ti, Mo, Nb, and Nd, and wherein the transparent electrode layer includes one or more elements selected from among In, Ga, Nb, Ta, W, Zn, Sn, Zr, Si, and F;

(4) The transparent electrode of any one of (1) to (3), wherein the metal layer includes a first metal portion formed of a first metal selected from the group consisting of Au, Pt, Ti, Mo, and Nd, and a second metal portion formed of a second metal selected from the group consisting of Ag, Al, Cr, Cu, and Nb, and wherein the first metal portion is disposed to cover the second metal part so that the second metal part is not exposed to the outside;

(5) The transparent electrode of any one of (1) to (4), wherein the current collector includes a first metal selected from the group consisting of Au, Pt, Ti, Mo, and Nd, and is formed to cover at least a portion of a side surface of the transparent electrode layer and an outermost surface of the conductive layer;

(6) The transparent electrode of any one of (1) to (5), wherein the transparent electrode layer is configured to have a film thickness of 50 nm or more and 200 nm or less; and (7) A measuring device including the transparent electrode of any one of (1) to (6).

According to the disclosure, the transparent electrode has physical and chemical durability for withstanding placement on the outermost surface of a device while securing transparency, in which the transparent electrode layer is placed on the outermost surface to be used as an electrode of the electrical measurement unit. Therefore, the electrical portion, which is conventionally opaque, may be made transparent, rendering it possible to superpose the electrical measurement unit and the optical measurement unit in a wearable device having a relatively small exterior area. Thus, according to the disclosure, the wearable device having the transparent electrode may have an increased degree of freedom in measuring methods while reducing design limitations, allowing for more optical measurements. Further, according to the disclosure, the use of the transparent electrode makes it possible to obtain optical biometric information in a broader area, enhancing the accuracy of measurement of biometric information. If the electrode portion includes only a metal electrode, the exterior is limited to an opaque metallic material from the viewpoint of design, but the use of the transparent electrode according to the disclosure enables application of a design to the lower layer of the electrode, thereby enhancing the design of the device.

According to an aspect of the disclosure, a transparent electrode is on an insulating substrate and is electrically connectable to an object in contact with the object. The transparent electrode includes: a conductive layer on the insulating substrate, the conductive layer including at least one of a metal layer or a metal oxide layer; a transparent electrode layer including $SnO_2$ as a main component; and a current collector on at least a portion of a side surface of the transparent electrode layer, the current collector being electrically connected to the transparent electrode layer and the conductive layer.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 9 is a table showing evaluation results of embodiments 1 to 3 in evaluation test 1 according to an embodiment;

FIG. 10 is a table showing evaluation results of embodiments 4 to 6 in evaluation test 1 according to an embodiment;

FIG. 11 is a table showing evaluation results of comparative examples 1 to 4 in evaluation test 1 according to an embodiment; and FIG. 12 is a table showing evaluation results of embodiment A, embodiment B, and embodiment C in evaluation test 2 according to an embodiment.

DETAILED DESCRIPTION

Figure 1:
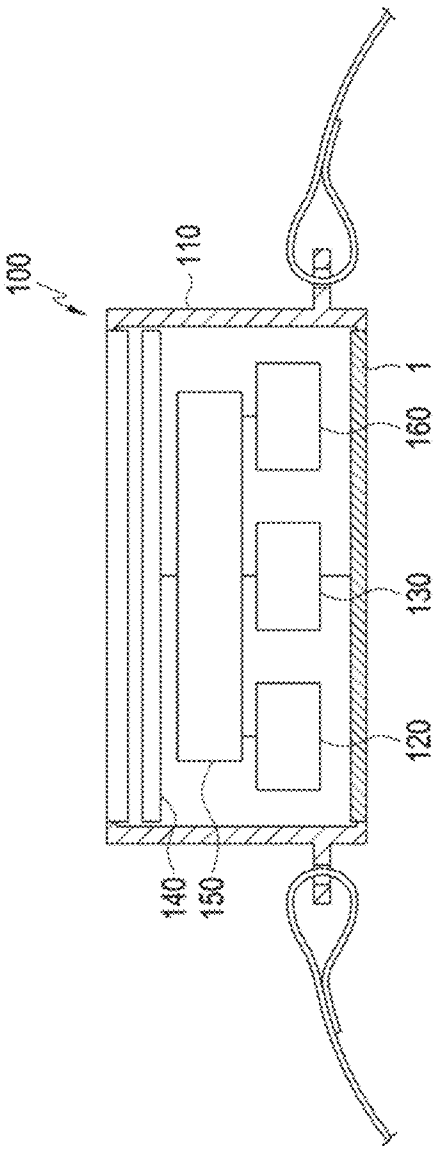
FIG. 1 is a concept view illustrating a wearable device which is a measuring device according to embodiments of the disclosure.

Hereinafter, modes for practicing the disclosure are described in detail with reference to the drawings. The embodiments shown here are illustrative to embody the technical spirit of the disclosure and do not limit the disclosure. Further, all other forms, embodiments, and operating techniques that may be implemented by one of ordinary skill in the art without departing from the gist of the disclosure are included in the scope and gist of the disclosure, and are included in the scope of the invention defined in the claims and equivalents thereof.

The terms as used in the disclosure are provided to merely describe specific embodiments, not intended to limit the scope of other embodiments. Singular forms include plural referents unless the context clearly dictates otherwise. The terms and words as used herein, including technical or scientific terms, may have the same meanings as generally understood by those skilled in the art. The terms as generally defined in dictionaries may be interpreted as having the same or similar meanings as or to contextual meanings of the relevant art. Unless otherwise defined, the terms should not be interpreted as ideally or excessively formal meanings. Even though a term is defined in the disclosure, the term should not be interpreted as excluding embodiments of the disclosure under circumstances.

The term “couple” and the derivatives thereof refer to any direct or indirect communication between two or more elements, whether or not those elements are in physical contact with each other. The terms “include” and “comprise”, and the derivatives thereof refer to inclusion without limitation. The term “or” is an inclusive term meaning “and/or”. The phrase “associated with,” as well as derivatives thereof, refer to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term “controller” refers to any device, system, or part thereof that controls at least one operation. The functionality associated with any particular controller may be centralized or distributed, whether locally or remotely. The phrase “at least one of,” when used with a list of items, means that different combinations of one or more of the listed items may be used, and only one item in the list may be needed. For example, “at least one of A, B, and C” includes any of the following combinations: A, B, C, A and B, A and C, B and C, and A and B and C, and any variations thereof. As an additional example, the expression “at least one of a, b, or c” may indicate only a, only b, only c, both a and b, both a and c, both b and c, all of a, b, and c, or variations thereof. Similarly, the term “set” means one or more. Accordingly, the set of items may be a single item or a collection of two or more items.

In one or more embodiments of the disclosure described below, a hardware approach is described as an example. However, since the one or more embodiments of the disclosure include technology that uses both hardware and software, the various embodiments of the present disclosure do not exclude a software-based approach.

In addition, in the disclosure, in order to determine whether a specific condition is satisfied or fulfilled, an expression of more than or less than may be used, but this is only a description for expressing an example, and does not exclude description of more than or equal to or less than or equal to. A condition described as ‘more than or equal to’ may be replaced with ‘more than’, a condition described as ‘less than or equal to’ may be replaced with ‘less than’, and a condition described as ‘more than or equal to and less than’ may be replaced with ‘more than and less than or equal to’.

Further, in the accompanying drawings, the scale, vertical and horizontal dimension ratio, and shape may be appropriately changed from those of the actual object for convenience of convenience, but they are merely examples and do not limit the interpretation of the disclosure.

Further, unless otherwise specified, operations and physical properties are measured under the conditions of room temperature (20° C. or higher and 25° C. or lower)/relative humidity of 40% RH or higher and 50% RH or lower.

Further, in the following description, the ordinal numbers, such as "first" and "second," are used for convenience, and do not define any specific order, unless otherwise specified.

In the following embodiments, a wristwatch-type wearable device is exemplified as a measuring device equipped with a transparent electrode 1 according to an embodiment. However, the disclosure may apply to other wearable devices than wristwatch-type wearable devices and other devices than wearable devices as long as they are capable of measuring information about an object to be measured, such as biometric information, as the measuring device equipped with the transparent electrode 1 of the disclosure.

A configuration of a transparent electrode 1 according to an embodiment of the disclosure is described appropriately with reference to FIGS. 1 to 8. However, FIGS. 1 to 8 regard a transparent electrode 1 and a measuring device according to an embodiment of the disclosure, and the transparent electrode 1 according to the embodiment is not limited to the configuration described with reference to the drawings.

FIG. 1 illustrates a portion of a wearable device 100 which is a measuring device including a transparent electrode 1 to measure predetermined information, such as biometric information.

<Wearable Device>

The wearable device 100 is put on a predetermined portion of the wearer, such as the wearer's arm, for use. Wearable device 100 has the function of measuring target information, such as biometric information. For example, a wristwatch-type wearable device may function as both a wristwatch and a measuring device.

Referring to FIG. 1, the wearable device 100 includes an optical measurement unit 120 that includes a light emitter configured to emit light and a light receiver configured to detect the intensity of infrared light reflected inside the living body to optically measure biometric information, such as heart rate and blood flow and an electrical measurement unit 130 that measures the biometric potential to electrically measure biometric information, such as body composition (body fat percentage or muscle mass), in a device body 110, a display unit 140 that is disposed on an upper surface of the device body 110, a controller 150 that overall controls the driving of each unit, and a power unit 160 that supplies driving power to each unit. The configuration of the wearable device 100 is not limited thereto, and may further include function implementing units for implementing other necessary functions, as device components.

The embodiments may be described and illustrated in terms of blocks, as shown in the drawings, which carry out a described function or functions. These blocks, which may be referred to herein as (the optical measurement units 120, the electrical measurement unit 130, the display unit 140, the power unit 160) or the like may be physically implemented by analog and/or digital circuits including one or more of a logic gate, an integrated circuit, a microprocessor, a microcontroller, a memory circuit, a passive electronic component, an active electronic component, an optical component, and the like, and may also be implemented by or driven by software and/or firmware (configured to perform the functions or operations described herein). The circuits may, for example, be embodied in one or more semiconductor chips, or on substrate supports such as printed circuit boards and the like. Circuits included in a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks. Likewise, the blocks of the embodiments may be physically combined into more complex blocks."

<Transparent Electrode 1>

Referring to FIG. 1, the transparent electrode 1 is installed in a predetermined position (e.g., on a lower surface of the device, as a mounting surface) of the wearable device 100. The transparent electrode 1 may be disposed in a position that may contact the wearer's skin.

Figure 2:
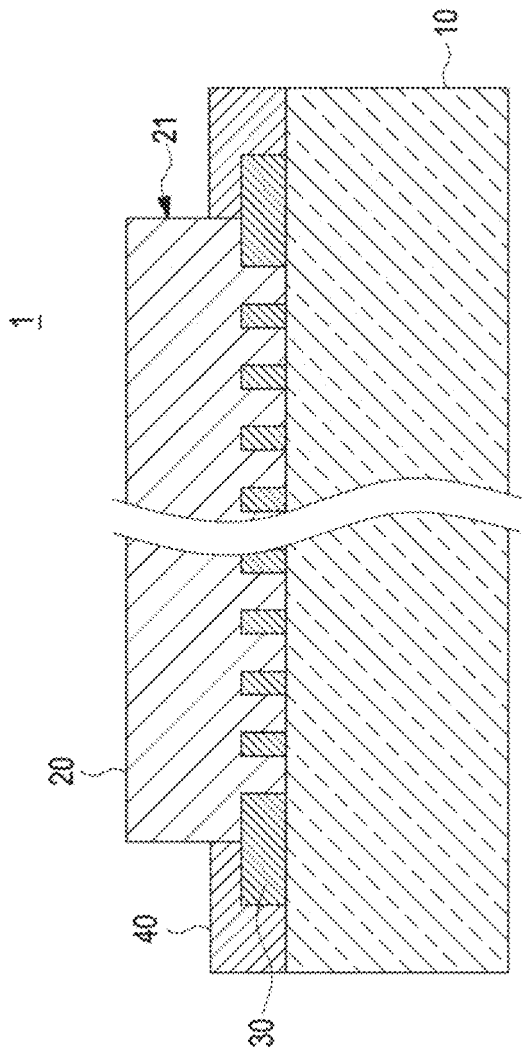
FIG. 2 is a cross-sectional view illustrating a transparent electrode according to an embodiment.
Figure 3:
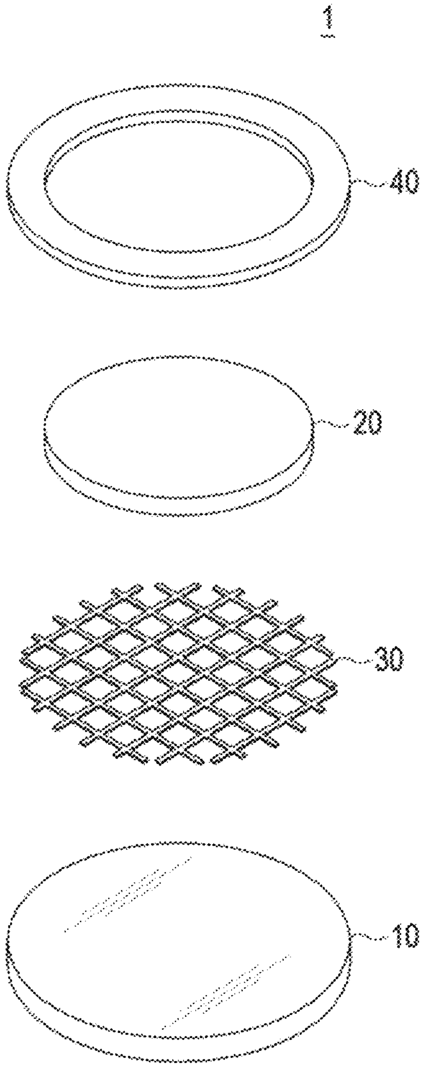
FIG. 3 is an exploded perspective view illustrating a transparent electrode.

Referring to FIG. 2, the transparent electrode 1 includes an insulating substrate 10, a transparent electrode layer 20, a conductive layer 30, and a current collector 40. Referring to FIGS. 2 and 3, in the transparent electrode 1, the conductive layer 30 is disposed on the insulating substrate 10, the transparent electrode layer 20 is disposed on the conductive layer 30, and the current collector 40 is disposed to cover at least a portion of a side surface 21 of the transparent electrode layer 20.

<Insulating Substrate 10>

In some embodiments, the insulating substrate 10 is formed of (or includes) an insulating material, such as alkali-free glass. The insulating substrate 10 blocks electrical connection between the transparent electrode 1 and internal devices of the wearable device 100.

<Transparent Electrode Layer 20>

In some embodiments, the transparent electrode layer 20 is formed of a conductive metal oxide and is (disposed) on the conductive layer 30. The transparent electrode layer 20 is electrically connected to the conductive layer 30. Referring to FIG. 1, the transparent electrode layer 20 is positioned on the outermost surface of the lower surface of the wearable device 100. Therefore, the transparent electrode 1 may come into contact with an object (such as the wearer's skin) and be electrically connected to the object.

In some embodiments, the transparent electrode layer 20 is formed of a material that has conductivity and transparency as well as physical and chemical durability. The transparent electrode layer 20 may be formed of a metal oxide that has $SnO_2$ as a main component to exhibit such properties. $SnO_2$ is chemically stable and has excellent durability as compared with metal oxide that uses $ITO_2O_3$ as a main component, such as metal oxide (ITO).

In some embodiments, the transparent electrode layer 20 may contain $SnO_2$ as a main component, and may further contain one or more elements (e.g., F) selected from among In, Ga, Nb, Ta, W, Zn, Sn, Zr, Si, and F.

When the transparent electrode layer 20 is formed only of $SnO_2$, durability is achieved, but the surface resistance increases. Increasing the film thickness for the purpose of decreasing the surface resistance may reduce transparency. In contrast, the transparent electrode layer 20 according to this embodiment further contains one or more of the above-described elements in addition to $SnO_2$ as the main component. Thus, when forming a film by sputtering, the surface roughness Ra may be lowered while controlling the average particle diameter in the film to be small. Further, as the surface roughness Ra of the transparent electrode layer 20 is lowered, the surface smoothness is enhanced. Accordingly, the transparent electrode layer 20 is less likely to wear out during friction occurs between the transparent electrode layer 20 and the wearer's skin, and may exhibit excellent durability.

From the viewpoint of durability and transparency, in some embodiments, the transparent electrode layer 20 has a film thickness of, for example, 50 nm or more and 200 nm or less, In some embodiments, the transparent electrode layer 20 has a film thickness of, for example, more than 60 nm and less than 200 nm. By controlling the thickness of the transparent electrode layer 20 within the above-mentioned range, durability, conductivity, and transparency of the transparent electrode may be secured. Here, if the film thickness of the transparent electrode layer 20 is less than 50 nm, durability and conductivity may decrease and the function as the transparent electrode 1 may deteriorate. Further, if the film thickness of the transparent electrode layer 20 exceeds 200 nm, the transmittance may decrease, and the measurement performance of the optical measurement unit 120 may not be sufficiently demonstrated.

From the viewpoint of durability, in some embodiments, the transparent electrode layer 20 may have a surface roughness Ra of 3.3 nm or less, a maximum height roughness Rz of 33 nm or less, and a film density of 6.8 $g/cm^{-3}$. The surface roughness Ra and the maximum height roughness Rz may be measured based on JIS B0601-2001. The film density may be measured, e.g., by X-ray reflectometry (XRR). By setting the surface roughness Ra, maximum height roughness Rz, and film density of the transparent electrode layer 20 to the above-mentioned values, wear due to friction against the wearer's skin may be suppressed and high durability may be maintained.

From the viewpoint of transparency, in some embodiments, the transparent electrode layer 20 may have an average transmittance of 80% or more for light having a wavelength range of 500 nm to 950 nm. The average transmittance may be measured based on JIS R3106-2019. As the transparent electrode layer 20 has an average transmittance of 80% or more, the optical measurement unit 120 may accurately obtain the necessary optical information. If the average transmittance of the transparent electrode layer 20 is less than 80%, optical information passing through the transparent electrode layer 20 decreases, making it difficult to obtain accurate information from the optical measurement unit 120.

From the viewpoint of conductivity, in some embodiments, the transparent electrode layer 20 may have a resistance of 200 Ω·cm or less between the central portion and the outer circumstantial end when viewed in plan view, and a surface resistance of the central portion of 220 Ω/sq or less. Thus, the transparent electrode layer 20 has higher surface resistance and resistance as compared to conventional metal electrodes, but has sufficient electrode performance in measuring biometric information, making it possible to replace it with conventional metal electrodes. Further, to obtain accurate electrical biometric information, the resistance of the transparent electrode itself may be low.

<Conductive Layer 30>

Referring to FIG. 2, the conductive layer 30 is electrically connected to the transparent electrode layer 20 and the current collector 40. The conductive layer 30 is interposed between the insulating substrate 10 and the transparent electrode layer 20. The conductive layer 30 is connected to the electrical measurement unit 130. The conductive layer 30 is formed of a metal layer 31 and/or a conductive metal oxide layer 32.

Figure 4:
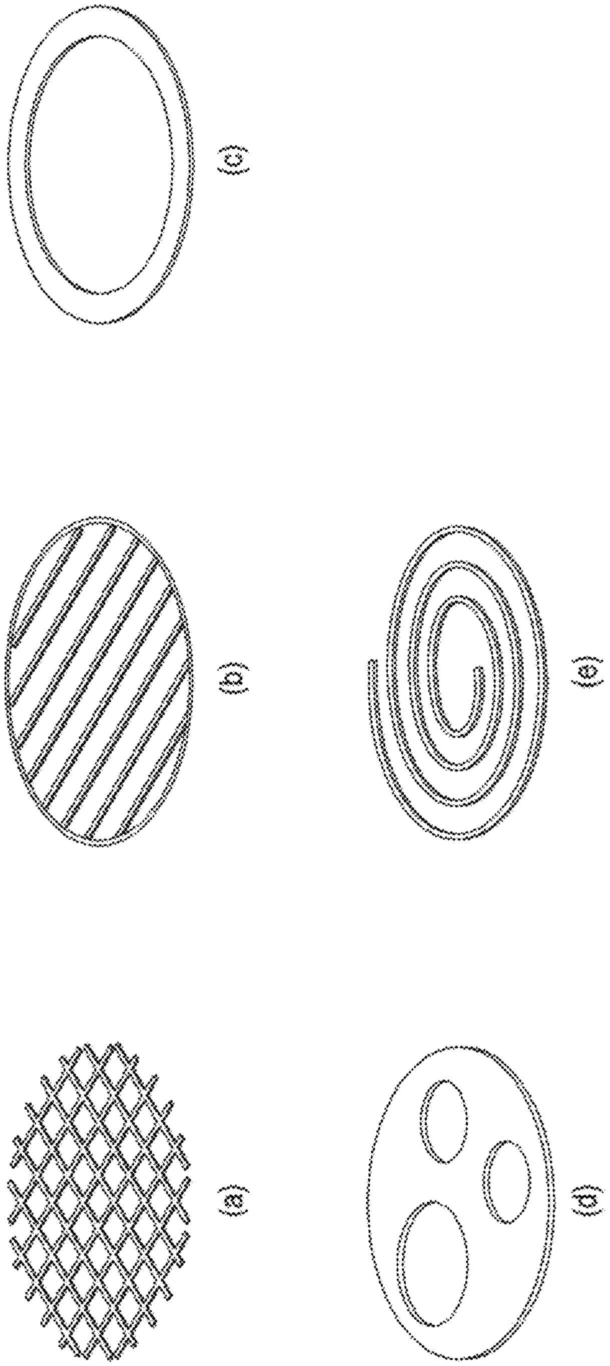
FIG. 4 is a view illustrating a modified example of a conductive layer of a transparent electrode.

When the conductive layer 30 is formed only of the metal layer 31 or formed in a stacked structure of the metal layer 31 and the metal oxide layer 32, from the viewpoint of transparency, when the film thickness exceeds 5 nm. In some embodiments, the projected area to the insulating substrate 10 is 30% or less of the area of the insulating substrate 10 when viewed in plan view. As shown in FIG. 4, the structure of the conductive layer 30 having such a projected area may include (a) a lattice shape, (b) a linear shape, (c) a ring shape, (d) a concave shape with a portion of the film cut out, and (e) a spiral shape in which an opening 33 for communicating with the insulating substrate 10 is formed.

Further, the shape and formation position of the conductive layer 30, the opening shape and opening size of the opening 33 are not limited to the shape shown in FIG. 4, and may be designed appropriately depending on the device configuration (the configuration or placement position of the mounted optical measurement unit 120) as long as the projected area to the insulating substrate 10 is 30% or less of the area of the insulating substrate 10.

The metal layer 31 may contain one or more elements selected from among Ag, Al, Cr, Cu, Au, Pt, Ti, Mo, Nb, and Nd. Among these metals, a metal selected from the group consisting of Au, Pt, Ti, Mo, and Nd may be classified as a "first metal," and a metal selected from the group consisting of Ag, Al, Cr, Cu, and Nb may be classified as a "second metal." Here, the "first metal" is a high-durability metal that has ease of processing and good durability but slightly poor conductivity. The "second metal" is a high-conductivity metal that has ease of processing and good conductivity but poor durability (in particular, poor acid/alkali resistance). The conductive layer 30 may include a first metal portion 31A (e.g., shown in FIG. 8) as a portion formed of the first metal and a second metal portion 31B (e.g., shown in FIG. 8) as a portion formed of the second metal.

When the conductive layer 30 includes only of the metal layer 31, it may be possible to obtain the advantages (high durability and high conductivity) of the two metals while compensating for the disadvantages (low durability and low conductivity) of the two metals by appropriately combining the two types of metals (first metal and second metal) appropriate as the conductive layer 30 and disposing the first metal portion 31A to surround the second metal portion 31B.

In addition to FIG. 2, FIGS. 5 to 8 show modified examples of the conductive layer 30.

Figure 5:
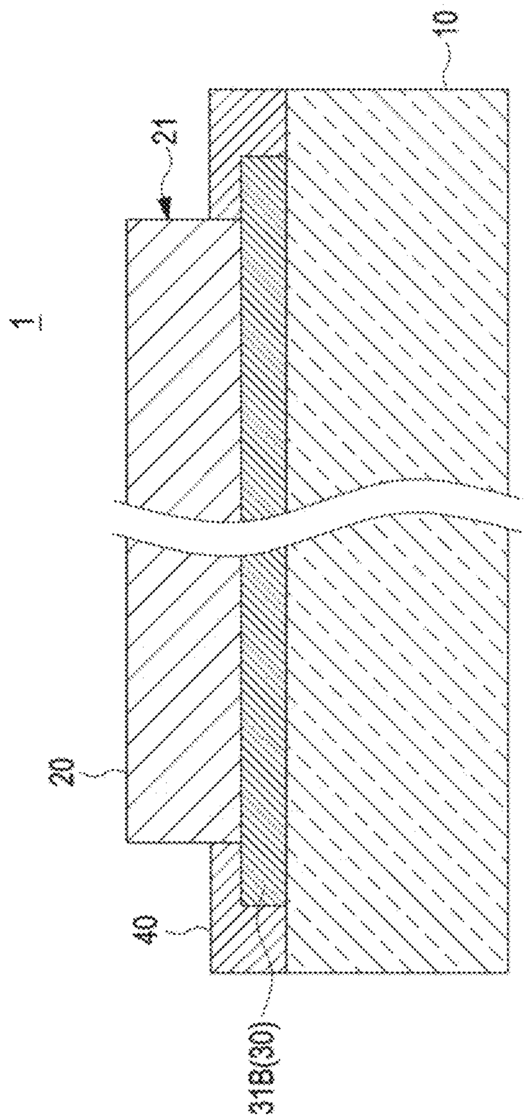
FIG. 5 is a cross-sectional view illustrating a transparent electrode according to modified example 1.

As shown in FIG. 5, the conductive layer 30 may have a stacked structure in which a conductive layer 30 formed of a second metal portion 31B is formed on an insulating substrate 10, and a transparent electrode layer 20 is formed on the conductive layer 30. In FIG. 5, since the conductive layer 30 is formed of the second metal portion 31B having poor durability, and the exposed portion of the outermost surface of the conductive layer 30 is covered with a current collector 40 formed of the first metal having excellent durability, it is not exposed to the outside. Further, since the transparent electrode 1 of FIG. 5 lacks an opening 33 in the conductive layer 30 formed only of a metal, the conductive layer 30 may be formed and may have a film thickness of 5 nm or less from the point of view of transparency.

Figure 6:
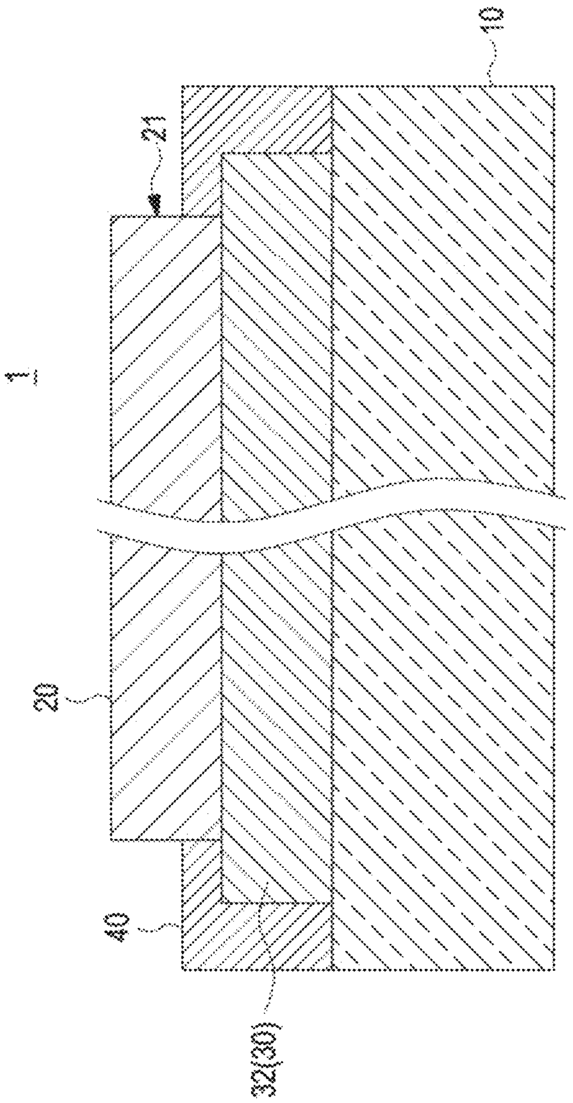
FIG. 6 is a cross-sectional view illustrating a transparent electrode according to modified example 2.

As shown in FIG. 6, the conductive layer 30 may have a stacked structure in which a conductive layer 30 formed of a metal oxide layer 32 formed of a metal oxide is formed on an insulating substrate 10, and a transparent electrode layer 20 is formed on the conductive layer 30. In FIG. 6, since the conductive layer 30 is formed of the metal oxide having poor durability, but the exposed portion of the outermost surface of the conductive layer 30 is covered with a current collector 40 formed of the first metal having excellent durability, it is not exposed to the outside. Therefore, the conductive layer 30 formed of the metal oxide layer 32 may enables use of a transparent conductive material having poor durability such as ITO.

Figure 7:
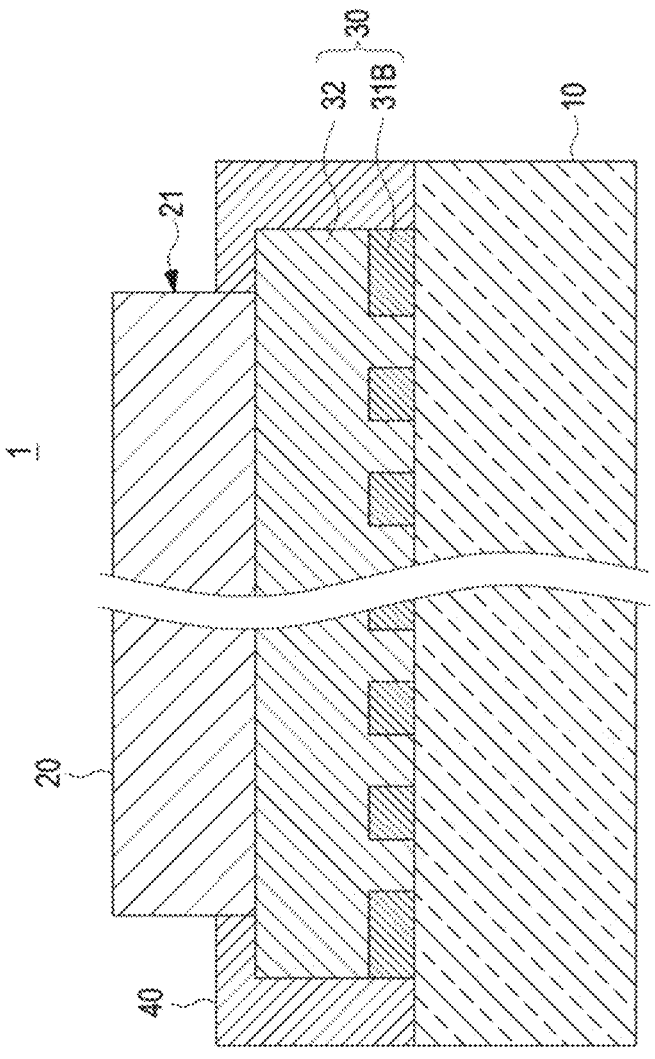
FIG. 7 is a cross-sectional view illustrating a transparent electrode according to modified example 3.

As shown in FIG. 7, the conductive layer 30 may have a stacked structure in which a conductive layer 30 having a dual-layer structure which has a second metal portion 31B having an opening 33 as a lower layer of a metal layer 31 and a metal oxide layer 32 as an upper layer, is formed on an insulating substrate 10, and a transparent electrode layer 20 is formed on the conductive layer 30. Further, a current collector 40 is formed of the first metal to cover the outer circumferential surface of the conductive layer 30. In FIG. 7, a lower surface of the conductive layer 30 is overall covered by the insulating substrate 10, and the exposed portion of the outermost surface is covered by the current collector 40 having excellent durability and is, thus, not exposed to the outside. Accordingly, in the conductive layer 30, the metal oxide layer 32 may be formed of a transparent conductive material having poor durability.

Figure 8:
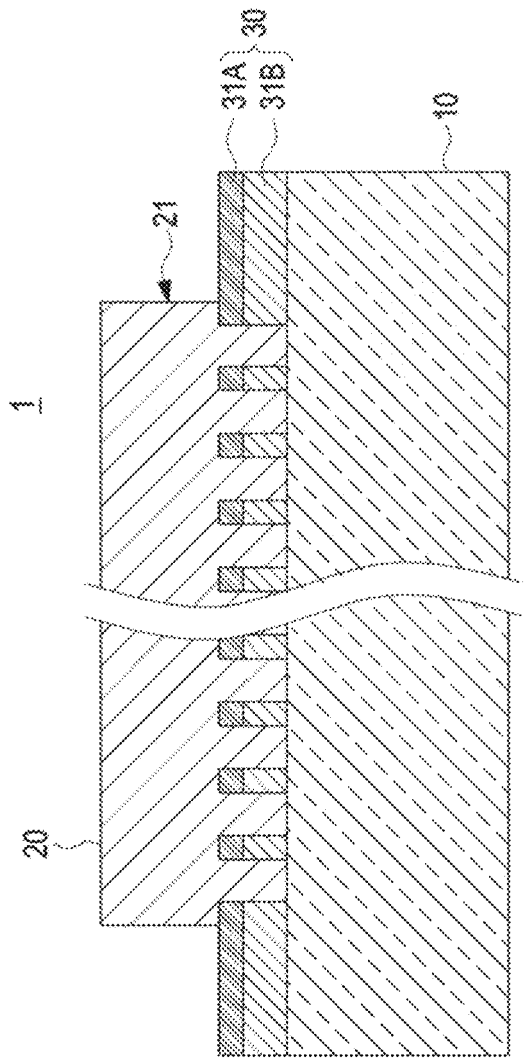
FIG. 8 is a cross-sectional view illustrating a transparent electrode according to modified example 4.

As shown in FIG. 8, the conductive layer 30 may have a stacked structure in which a conductive layer 30 having a dual-layer structure which has a second metal portion 31B as a lower layer and a first metal portion 31A as an upper layer, is formed on an insulating substrate 10, and a transparent electrode layer 20 is formed on the conductive layer 30. The conductive layer 30 is disposed so that the second metal portion 31B formed of the second metal is surrounded by the first metal portion 31A formed of the first metal. Accordingly, as shown in FIG. 8, in the conductive layer 30, when forming the electrode, the transparent electrode layer 20 is put in the opening 33 so that the portion of the second metal portion 31B is not exposed to the outside. Therefore, the transparent electrode 1 in FIG. 8 may maintain the conductivity of the second metal portion 31B while compensating for the durability which is a drawback to the second metal, by preventing exposure of the second metal portion 31B. Further, in FIG. 8, the conductive layer 30 is formed of metal and is disposed to cover a portion of the side surface 21 of the transparent electrode layer 20, fulfilling the function of the current collector 40. This eliminates the need for forming a separate current collector 40, simplifying the configuration.

In some embodiments, the film thickness of the conductive layer 30 may be 5 nm or more and 100 nm or less from the viewpoint of transparency and conductivity and, given transparency, the thinner the better. Further, the film thickness of the conductive layer 30 may be appropriately set by a combination of the metal layer 31 and/or the metal oxide layer 32 while considering, e.g., transparency.

<Current Collector 40>

The current collector 40 is disposed to cover at least a portion of the side surface 21 of the transparent electrode layer 20. As shown in FIG. 2, the current collector 40 may be disposed on the edge of the conductive layer 30 and may be disposed to cover a portion of the side surface 21 of the transparent electrode layer 20 over the entire circumference. The current collector 40 reduces connection resistance between the transparent electrode layer 20 and the internal circuit (wristwatch, wearable device, etc.).

The constituent material of the current collector 40 is a metal material capable of electrical connection with the transparent electrode layer 20 and the conductive layer 30. Specifically, as the constituent material of the current collector 40, the first metal (a metal selected from the group consisting of Au, Pt, Ti, Mo, and Nd) used in the current collector 40 may be used. The current collector 40 may obtain high durability by being formed of the first metal. Accordingly, if the current collector 40 is formed to cover the outermost surface of the conductive layer 30 while covering at least a portion of the side surface of the transparent electrode layer 20, the durability of the transparent electrode 1 may be increased.

As a method for forming the transparent electrode layer 20, the conductive layer 30, and the current collector 40 that constitute the transparent electrode 1, a method may be selected depending on the forming material, as well as vacuum deposition, physical vapor deposition (PVD), chemical vapor deposition (CVD), and spray pyrolysis deposition (SPD). In particular, in some embodiments, the PVD method may form a dense thin film.

As described above, the transparent electrode 1 according to an embodiment is formed on an insulating substrate 1 and electrically connected to an object in contact with the object. In some embodiments, the transparent electrode 1 has a stacked structure in which a transparent electrode layer 20 having $SnO_2$ as a main component and a conductive layer 30 formed of a metal layer 31 and/or a metal oxide layer 32 having conductivity are stacked in an order thereof from an outermost surface side. At least a portion of a side surface 21 of the transparent electrode layer 20 is covered with a current collector 40 electrically connected to the transparent electrode layer 20 and the conductive layer 30.

Further, in the transparent electrode 1 according to an embodiment, the metal layer 31 of the conductive layer 30 may be formed so that a projected area to the insulating substrate 10 is 30% of an area of the insulating substrate 10 or less when viewed in plan view when a film thickness exceeds 5 nm.

Further, in the transparent electrode 1 according to an embodiment, the metal layer 31 may contain one or more elements selected from among Ag, Al, Cr, Cu, Au, Pt, Ti, Mo, Nb, and Nd, and the transparent electrode layer 20 contains one or more elements selected from among In, Ga, Nb, Ta, W, Zn, Sn, Zr, Si, and F.

Further, in the transparent electrode 1 according to an embodiment, the metal layer 31 may include a first metal portion 31A formed of a first metal selected from the group consisting of Au, Pt, Ti, Mo, and Nd, and a second metal portion 31B formed of a second metal selected from the group consisting of Ag, Al, Cr, Cu, and Nb, and the first metal portion 31A is disposed to prevent exposure of the second metal portion 31B.

Further, in the transparent electrode 1 according to an embodiment, the current collector 40 may be formed of a first metal selected from the group consisting of Au, Pt, Ti, Mo, and Nd, and is formed to cover at least a portion of a side surface 21 of the transparent electrode layer 20 and an outermost surface of the conductive layer 30.

Further, in the transparent electrode according to an embodiment, the transparent electrode layer 20 may have a film thickness of 50 nm or more and 200 nm or less.

Further, the above-described transparent electrode 1 may be provided in an electronic device, such as the wearable device 100, which has a measuring function and includes the optical measurement unit 120 and the electrical measurement unit 130.

By such a configuration, the transparent electrode layer 20 which has physical and chemical durability may be disposed on the outermost surface. Thus, as it is used as an electrode of the electrical measurement unit 130, the electrode portion (which is conventionally formed of an opaque metal) may be made transparent. Therefore, it is possible to superpose the electrical measurement unit 130 and the optical measurement unit 120 in a wearable device 100 having a relatively small exterior area. Thus, the wearable device 100 having the transparent electrode 1 may have an increased degree of freedom in measuring methods while reducing design limitations, allowing for more optical measurements. Further, the use of the transparent electrode 1 according to the disclosure in, e.g., the wearable device 100 makes it possible to obtain optical biometric information in a broader area, enhancing the accuracy of measurement of biometric information. If the electrode portion includes only a metal electrode as in the conventional art, the exterior is limited to an opaque metallic material from the viewpoint of design, but the use of the transparent electrode 1 according to the disclosure enables application of a design to the lower layer of the electrode, thereby enhancing the design of the device.

The effects of the disclosure are described using embodiments and comparative examples as follows. However, the technical scope of the disclosure is not limited to the following embodiments.

[Evaluation Test 1]

Performance tests were conducted on each sample of the embodiments and comparative examples shown below.

<Preparation of Samples>

Samples according to embodiments (embodiments 1 to 6) and samples according to comparative examples (comparative examples 1 to 4) were prepared according to the following processes.

Preparation of Sample According to Embodiment 1

In the sample according to embodiment 1, a conductive layer was formed on an insulating substrate formed of alkali-free glass having a diameter of 26 mm, and a transparent electrode layer was formed thereon (shape shown in FIG. 8). The conductive layer and transparent electrode layer were formed by sputtering. A DC magnetron sputtering device (commercially available from Showa Shinkusho Co., Ltd.) was used to form the conductive layer, and a sputtering device (commercially available from Toshima Seisakusho Co., Ltd.) was used to form the transparent electrode layer. The conductive layer was formed by introducing Ar gas at an in-device vacuum level of $10^{-3}$ Pa or less, a pressure of 0.4 Pa, and a discharge power of DC30W. The transparent electrode layer was formed by introducing Ar gas at an in-device vacuum level of $10^{-3}$ Pa or less, a pressure of 0.4 Pa, and a discharge power of RF100W. Further, the substrate during film formation was heated to 100° C. to form a film. The conductive layer was formed by laminating a first metal (Mo) with a film thickness of 20 nm on a second metal (Al) with a film thickness of 30 nm. The conductive layer was made into a lattice shape by arranging a plurality of openings of 2 mm×2 mm in four directions in a matrix shape. As the transparent electrode layer, a thin film that contains $SnO_2$ as the main component was formed. As the samples according to embodiment 1, five types of samples with film thicknesses of 30 nm, 60 nm, 100 nm, 200 nm, and 300 nm were prepared on the conductive layer. The conductive layer was also used as a current collector. The sample according to embodiment 1 has the shape shown in FIG. 8.

Preparation of Sample According to Embodiment 2

In the sample according to embodiment 2, a conductive layer was formed on an insulating substrate formed of alkali-free glass having a diameter of 26 mm, and a transparent electrode layer was formed thereon. The conductive layer and the transparent electrode layer were formed in the same manner as embodiment 1. The conductive layer was formed of a second metal (Al) with a film thickness of 3 nm without forming an opening. The transparent electrode layer was formed of $SnO_2$. As the samples according to embodiment 2, five types of samples with film thicknesses of 30 nm, 60 nm, 100 nm, 200 nm, and 300 nm were prepared on the conductive layer. The current collector was formed of the first metal (Mo) to cover the conductive layer not to be exposed. The sample according to embodiment 2 has the shape shown in FIG. 5.

Preparation of Sample According to Embodiment 3

In the sample according to embodiment 3, a conductive layer was formed on an insulating substrate formed of alkali-free glass having a diameter of 26 mm, and a transparent electrode layer was formed thereon. The conductive layer and the transparent electrode layer were formed in the same manner as embodiment 1. The conductive layer was formed of a second metal (Al) with a film thickness of 30 nm. The conductive layer was made into a lattice shape by arranging a plurality of openings of 2 mm×2 mm in four directions in a matrix shape. The transparent electrode layer was formed of $SnO_2$. As the samples according to embodiment 3, five types of samples with film thicknesses of 30 nm, 60 nm, 100 nm, 200 nm, and 300 nm were prepared on the conductive layer. The current collector was formed of the first metal (Mo) to cover the conductive layer not to be exposed. The sample according to embodiment 3 has the shape shown in FIG. 2.

Preparation of Sample According to Embodiment 4

In the sample according to embodiment 4, a conductive layer was formed on an insulating substrate formed of alkali-free glass having a diameter of 26 mm, and a transparent electrode layer was formed thereon. The conductive layer and the transparent electrode layer were formed by sputtering as embodiment 1. The conductive layer was formed of a metal oxide (ITO) with a film thickness of 100 nm without forming an opening. The transparent electrode layer was formed of $SnO_2$. As the samples according to embodiment 4, five types of samples with film thicknesses of 30 nm, 60 nm, 100 nm, 200 nm, and 300 nm were prepared on the conductive layer. The current collector was formed of the first metal (Mo) to cover the conductive layer not to be exposed. The sample according to embodiment 4 has the shape shown in FIG. 6.

Preparation of Sample According to Embodiment 5

In the sample according to embodiment 5, a conductive layer was formed on an insulating substrate formed of alkali-free glass having a diameter of 26 mm, and a transparent electrode layer was formed thereon. The conductive layer and the transparent electrode layer were formed by sputtering as in embodiment 1. The conductive layer was formed by laminating a metal oxide (ITO) with a film thickness of 100 nm on a second metal (Al) with a film thickness of 30 nm. The layer formed of the second metal was made into a lattice shape by arranging a plurality of openings of 2 mm×2 mm in four directions in a matrix shape. The transparent electrode layer was formed of $SnO_2$. As the samples according to embodiment 5, five types of samples with film thicknesses of 30 nm, 60 nm, 100 nm, 200 nm, and 300 nm were prepared on the conductive layer. The current collector was formed of the first metal (Mo) to cover the conductive layer not to be exposed. The sample according to embodiment 5 has the shape shown in FIG. 7.

Preparation of Sample According to Embodiment 6

In the sample according to embodiment 6, a conductive layer was formed on an insulating substrate formed of alkali-free glass having a diameter of 26 mm, and a transparent electrode layer was formed thereon. The conductive layer and the transparent electrode layer were formed by sputtering as in embodiment 1. The conductive layer was formed by laminating a first metal (Mo) with a film thickness of 20 nm on a second metal (Al) with a film thickness of 30 nm. The conductive layer was made into a lattice shape by arranging a plurality of openings of 2 mm×2 mm in four directions in a matrix shape. The transparent electrode layer was formed by containing $SnO_2$ as a main component and adding F ($SnO_2$: 95 parts by mass, F: 5 parts by mass). As the samples according to embodiment 6, five types of samples with film thicknesses of 30 nm, 60 nm, 100 nm, 200 nm, and 300 nm were prepared on the conductive layer. The conductive layer was also used as a current collector. The sample according to embodiment 6 has the shape shown in FIG. 8 as in embodiment 1.

Preparation of Sample According to Comparative Example 1

In the sample according to comparative example 1, a conductive layer was formed on an insulating substrate formed of alkali-free glass having a diameter of 26 mm, and a transparent electrode layer was formed thereon. The conductive layer and the transparent electrode layer were formed by sputtering as in embodiment 1. The conductive layer was formed of a second metal (Al) with a film thickness of 30 nm. The layer formed of the second metal was made into a lattice shape by arranging a plurality of openings of 2 mm×2 mm in four directions in a matrix shape. The transparent electrode layer was formed of $SnO_2$. As the samples according to embodiment 5, five types of samples with film thicknesses of 30 nm, 60 nm, 100 nm, 200 nm, and 300 nm were prepared on the conductive layer. The conductive layer was also used as a current collector. The sample according to comparative example 1 has a shape that lacks the first metal layer in the conductive layer according to embodiment 1.

Preparation of Sample According to Comparative Example 2

In the sample according to comparative example 2, a conductive layer was formed on an insulating substrate formed of alkali-free glass having a diameter of 26 mm, and a transparent electrode layer was formed thereon. The conductive layer and the transparent electrode layer were formed by sputtering as in embodiment 1. The conductive layer was formed of a metal oxide (ITO) with a film thickness of 100 nm. The transparent electrode layer was formed of $SnO_2$. As the samples according to comparative example 2, five types of samples with film thicknesses of 30 nm, 60 nm, 100 nm, 200 nm, and 300 nm were prepared on the conductive layer. The conductive layer was also used as a current collector. The sample according to comparative example 2 has a shape that lacks the current collector in embodiment 4.

Preparation of Sample According to Comparative Example 3

In the sample according to comparative example 3, only a transparent electrode layer was formed of $SnO_2$ on an insulating substrate formed of alkali-free glass having a diameter of 26 mm without forming a conductive layer. The transparent electrode layer were formed by sputtering as in embodiment 1. As the samples according to comparative example 3, five types of samples with film thicknesses of 30 nm, 60 nm, 100 nm, 200 nm, and 300 nm were prepared on the insulating substrate. The sample according to comparative example 3 has a shape that lacks the conductive layer in comparative example 2.

Preparation of Sample According to Comparative Example 4

In the sample according to comparative example 4, only a conductive layer formed of a metal oxide (ITO) having a film thickness of 100 nm was formed without forming a transparent electrode layer on an insulating substrate formed of alkali-free glass with a diameter of 26 mm. The conductive layer was formed by sputtering as in embodiment 1. The sample according to comparative example 4 has a shape that lacks the transparent electrode layer in comparative example 2.

<What Tested>

A physical durability test, a chemical durability test, a conductivity test, and a transparency test were performed on each of the sample according to the embodiments and comparative examples, prepared in the above-described order.

<Physical Durability Test>

For the physical durability test, a ϕ6 mm eraser was placed on the surface of the transparent electrode layer of each sample with a load of 1 kg applied, and was reciprocated 3,000 times at a moving distance of 15 mm, a moving speed of 40 reciprocations/min, using a reciprocating friction tester (product name: TYPE30S, commercially available from Shinto Chemical Co., Ltd.). As the evaluation method, the presence or absence of scratches on the exterior of the electrode was identified with the naked eye and under a microscope after the test. The evaluation criteria are as follows.

○: No scratches observed with the naked eye and under a microscope

Δ: No scratches observed with the naked eye but scratches observed under a microscope x: Scratches observed with the naked eye and under a microscope <Chemical Durability Test>

In the chemical durability test, the transparent electrode was placed in a solution adjusted to pH 4.6 (buffer pH 4.6 ($C_8H_5KO_4$—NaOH) (commercially available from Tokyo Kasei Kogyo Co., Ltd.) and left for 48 hours so that there were parts immersed and parts not immersed, and changes in appearance before and after the test were observed. The evaluation criteria are as follows.

○: A change observed x: No change observed.

<Conductivity Test>

In the conductivity test, the surface resistance (Ω/sq) was measured by 4 terminals in the central portion of the sample using a surface resistance meter (product name: Loresta-GX MCP-T700, commercially available from Nitto Seiko Analytech Co., Ltd.). Further, the resistance (Ω) of the portion (about 15 mm) between the central portion of the sample and the current collector was measured using a resistance meter (product name: RM3548, commercially available from Nippon Denki Co., Ltd.). The evaluation criteria are as follows.

Surface Resistance

○: Less than 200 Ω/sq x: 200 Ω/sq or more

Resistance Between Center and Current Collector

○: Less than 220Ω x: 220Ω or more.

<Transparency Test>

For the transparency test, the average value of the transmittances of each sample at wavelengths of 530 nm, 660 nm, and 940 nm was calculated using an ultraviolet-visible spectrophotometer (product name: UV-1900, commercially available from Shimazu Seisakusho Co., Ltd.). The evaluation criteria are as follows.

○: Average transmittance 80% or more

Δ: Average transmittance 70% or more to less than 80% x: Average transmittance less than 70%.

<Results>

FIG. 9 illustrates the specifications and results of evaluation test 1 for the samples according to embodiments 1 to 3. FIG. 10 illustrates the specifications and results of evaluation test 1 for the samples according to embodiments 4 to 6. FIG. 11 illustrates the specifications and results of evaluation test 1 for the samples according to comparative examples 1 to 4.

As shown in each table in FIG. 9 or FIG. 10, it was identified that the sample having the transparent electrode layer with a film thickness of 100 nm according to embodiment 1, the samples having the transparent electrode layers with film thicknesses of 60 nm and 100 nm according to embodiment 2, the sample having the transparent electrode layer with a film thickness of 100 nm according to embodiment 3, and the samples having the transparent electrode layers with film thicknesses of 30 nm, 60 nm, and 100 nm according to embodiments 4 and 5 all are evaluated as "○" in the physical durability test, chemical durability test, conductivity test, and transparency test, and ensure good quality for products. It may also be identified from the results of embodiments 1 to 6 that chemical durability may be secured in the exposed portion of the conductive layer (current collector) by coating the second metal of the conductive layer with the first metal, that transparency may be secured by setting the film thickness of the transparent electrode layer to be 50 nm or more and 200 nm or less, that transparency may be secured regardless of the film thickness of the conductive layer by forming an opening in the conductive layer, that chemical durability may be secured by forming the current collector with a high-durability first metal and coating the conductive layer, and that deterioration of physical durability may be prevented although the film is thickened without significantly growing crystal particles in the film by adding a predetermined additive to the transparent electrode layer containing $SnO_2$ as a main component.

As shown in the table of FIG. 11, it may be identified that comparative examples 1 to 4 all exhibit poor chemical durability or conductivity results, failing to meet product quality. Further, it may be identified from the results of comparative examples 1 to 4 that as the thickness of the transparent electrode layer reduces, transparency increases, but physical durability and conductivity decrease, that as the thickness of the transparent electrode layer increases, conductivity increases, but transparency decreases, that if the conductive layer formed of the second metal is used as a current collector, chemical durability may not be secured because the second metal with poor durability is exposed, that if the film thickness of the transparent electrode layer is 60 nm or less due to a step in the opening of the conductive layer, physical durability may not be secured due to insufficient coat of the conductive layer, that if the film thickness of the transparent electrode layer is 200 nm or more, transparency decreases, that if the conductive layer (metal oxide) is used as a current collector, chemical durability is not secured due to exposure of the metal oxide, that it may be possible to secure durability but not conductivity only with the transparent electrode layer, and that it is hard to secure chemical durability only with the conductive layer.

[Evaluation Test 2]

Performance tests were conducted on each sample of the embodiments and comparative examples shown below.

<Preparation of Samples>

The transparent electrode layers according to embodiments A and B were both formed by sputtering.

The transparent electrode layer according to comparative example C was formed by spray pyrolysis deposition.

The surface roughness (Ra) and maximum height roughness (Rz) of each sample were analyzed using a scanning probe microscope (SPM) (product name: SPM-9700HT, commercially available from Shimazu Seisakusho Co., Ltd.). The average particle size was measured using a scanning electron microscope SEM device (product name: Dual Beam FIB Helios 5 UC, commercially available from Thermo Scientific). The film density was measured by X-ray reflectivity (XRR) using a fully automatic sample horizontal multi-purpose X-ray diffraction device (product name: SmartLab, commercially available from Rigaku Co., Ltd.).

<What Tested>

In evaluation test 2, similar to the physical durability test in evaluation test 1, a ϕ6 mm eraser was placed on the surface of the transparent electrode layer of each sample with a load of 1 kg applied, and was reciprocated 3,000 times at a moving distance of 15 mm and a moving speed of 40 reciprocations/min. As the evaluation method, the presence or absence of scratches on the exterior of the electrode was identified with the naked eye and under a microscope after the test. The evaluation criteria are as follows.

○: No scratches observed with the naked eye and under a microscope x: Scratches observed with the naked eye and under a microscope <Results>

FIG. 12 shows the results of evaluation test 2. It was identified that good durability was obtained in both embodiments A and B. In contrast, it was identified that comparative example C had poor durability results, failing to meet product quality. It was identified therefrom that the transparent electrode had excellent durability by preparing the transparent electrode layer of the transparent electrode to have a surface roughness Ra of 3.3 nm or less, a maximum height roughness Rz of 33 nm or less, and a film density of 6.8 $g/cm^{-3}$ from the viewpoint of durability.

What is claimed is:

1. A transparent electrode disposed on an insulating substrate and electrically connectable to an object in contact with the object, the transparent electrode comprising:

a conductive layer disposed on the insulating substrate, the conductive layer comprising a metal oxide layer having at least one of a metal layer or a metal oxide layer;

a transparent electrode layer comprising $SnO_2$ as a main component; and a current collector disposed, in a cross-sectional view, on at least a portion of a lateral surface of the transparent electrode layer, the current collector being electrically connected to the transparent electrode layer and the conductive layer.

2. The transparent electrode of claim 1, wherein, when the conductive layer comprises the metal layer and the metal layer of the conductive layer has a film thickness of more than 5 nm, a projected area with respect to the insulating substrate when looking down at the metal layer is 30% or less of the area of the insulating substrate.

3. The transparent electrode of claim 2, wherein the projected area of the metal layer has a lattice shape, a linear shape, a ring shape, a concave shape with a portion cut out, or a spiral shape.

4. The transparent electrode of claim 1, wherein the metal layer comprises at least one of Ag, Al, Cr, Cu, Au, Pt, Ti, Mo, Nb, or Nd, and wherein the transparent electrode layer comprises at least one of In, Ga, Nb, Ta, W, Zn, Sn, Zr, Si, or F.

5. The transparent electrode of claim 1, wherein the metal layer comprises a first metal portion formed of a first metal selected from Au, Pt, Ti, Mo, and Nd, and a second metal portion formed of a second metal selected from Ag, Al, Cr, Cu, and Nb, and wherein the first metal portion is configured to cover the second metal part so that the second metal portion is not exposed to an outside of the transparent electrode.

6. The transparent electrode of claim 1, wherein the current collector comprises a first metal selected from Au, Pt, Ti, Mo, and Nd, and wherein the first metal is configured to cover, in a cross-sectional view, at least a portion of a lateral surface of the transparent electrode layer and an outermost surface of the conductive layer.

7. The transparent electrode of claim 1, wherein the transparent electrode layer is configured to have a film thickness of 50 nm or more and 200 nm or less.

8. A measuring device comprising an insulating substrate and a transparent electrode disposed on the insulating substrate and electrically connectable to an object in contact with the object, the transparent electrode comprising:

a conductive layer on the insulating substrate, the conductive layer comprising at least one of a metal layer or a metal oxide layer;

a transparent electrode layer comprising $SnO_2$ as a main component; and a current collector disposed, in a cross-sectional view, on at least a portion of a lateral surface of the transparent electrode layer, the current collector being electrically connected to the transparent electrode layer and the conductive layer.

9. The measuring device of claim 8, wherein the measuring device is a wearable device.

* * * * *